US005444373A

United States Patent [19]
Johnson et al.

[11] Patent Number: 5,444,373
[45] Date of Patent: Aug. 22, 1995

[54] BIOMAGNETOMETER WITH SELECTABLE PICKUP COIL ARRAY

[75] Inventors: Richard T. Johnson; Laurence Warden, both of San Diego, Calif.

[73] Assignee: Biomagnetic Technologies, Inc., San Diego, Calif.

[21] Appl. No.: 248,533

[22] Filed: May 23, 1994

Related U.S. Application Data

[63] Continuation of Ser. No. 831,902, Feb. 6, 1992, abandoned.

[51] Int. Cl.⁶ .............. G01R 33/035; A61B 5/05; G08C 15/06; H04J 3/00
[52] U.S. Cl. .................. 324/248; 128/653.1; 340/870.31; 370/112; 324/247
[58] Field of Search ........... 324/242, 243, 244, 247, 324/248, 260; 128/653.1; 370/112; 340/825.03, 825.1, 825.11, 870.13

[56] References Cited

U.S. PATENT DOCUMENTS

| 3,241,058 | 3/1966 | Quittner | 324/242 |
| 4,489,274 | 12/1984 | Berlincourt . | |
| 4,700,135 | 10/1987 | Hoenig | 324/248 |
| 4,771,239 | 9/1988 | Hoenig | 324/248 |
| 4,977,896 | 12/1990 | Robinson et al. | 324/248 X |
| 5,047,719 | 9/1991 | Johnson et al. | 324/242 |
| 5,093,618 | 3/1992 | Goto et al. | 324/248 |

FOREIGN PATENT DOCUMENTS

0200080A1 12/1986 European Pat. Off. .
0408302A3 1/1991 European Pat. Off. .

OTHER PUBLICATIONS

Anon., "Squid Multiplexing Technique", *IBM Technical Disclosure Bulletin*, vol. 29, No. 6, pp. 2434–2435 (Nov. 1986).
Anon., "Squid Multiplexing Method", *IBM Technical Disclosure Bulletin*, vol. 29, No. 6, p. 2513 (Nov. 1986).
S. Erne et al., "The Positioning Problem in Biomagnetic Measurements: A Solution for Arrays of Superconducting Sensors," *IEEE Trans. on Magnetics*, vol. MAG-23, No. 2, pp. 1319–1322 (Mar. 1987).
H. E. Hoenig et al., "Biomagnetic multichannel system with integrated Squids and first order gradiometers operating in a shielded room," *Cryogenics*, vol. 29, pp. 809–813 (Aug. 1989).
Jukka Knuutila, "Multi-Squid Magnetometers for Neuromagntic Research," *Cryogenics*, vol. 30, pp. 1–8 (Sep. 1990).

*Primary Examiner*—Gerard R. Strecker
*Attorney, Agent, or Firm*—Gregory Garmong

[57] ABSTRACT

A biomagnetometer comprises an array of biomagnetic sensors, the array comprising a first plurality of magnetic field pickup coils, and a second plurality of detectors, each of which receives a pickup coil output from a pickup coil. There is a third plurality of signal processors, each of which receives an output from a detector, the third plurality of signal processors being fewer in number than the first plurality of pickup coils. The biomagnetometer further includes a selector that selects a subset of pickup coils, equal in number to the third plurality of signal processors, from the first plurality of pickup coils for signal processing by the signal processors. This biomagnetometer permits the placement of a very large array of relatively inexpensive pickup coils adjacent to a subject, and then processing information from subsets of that large array selected to optimize the gathering of data, while maintaining the cost of the signal processing electronics at a more economical level.

15 Claims, 3 Drawing Sheets

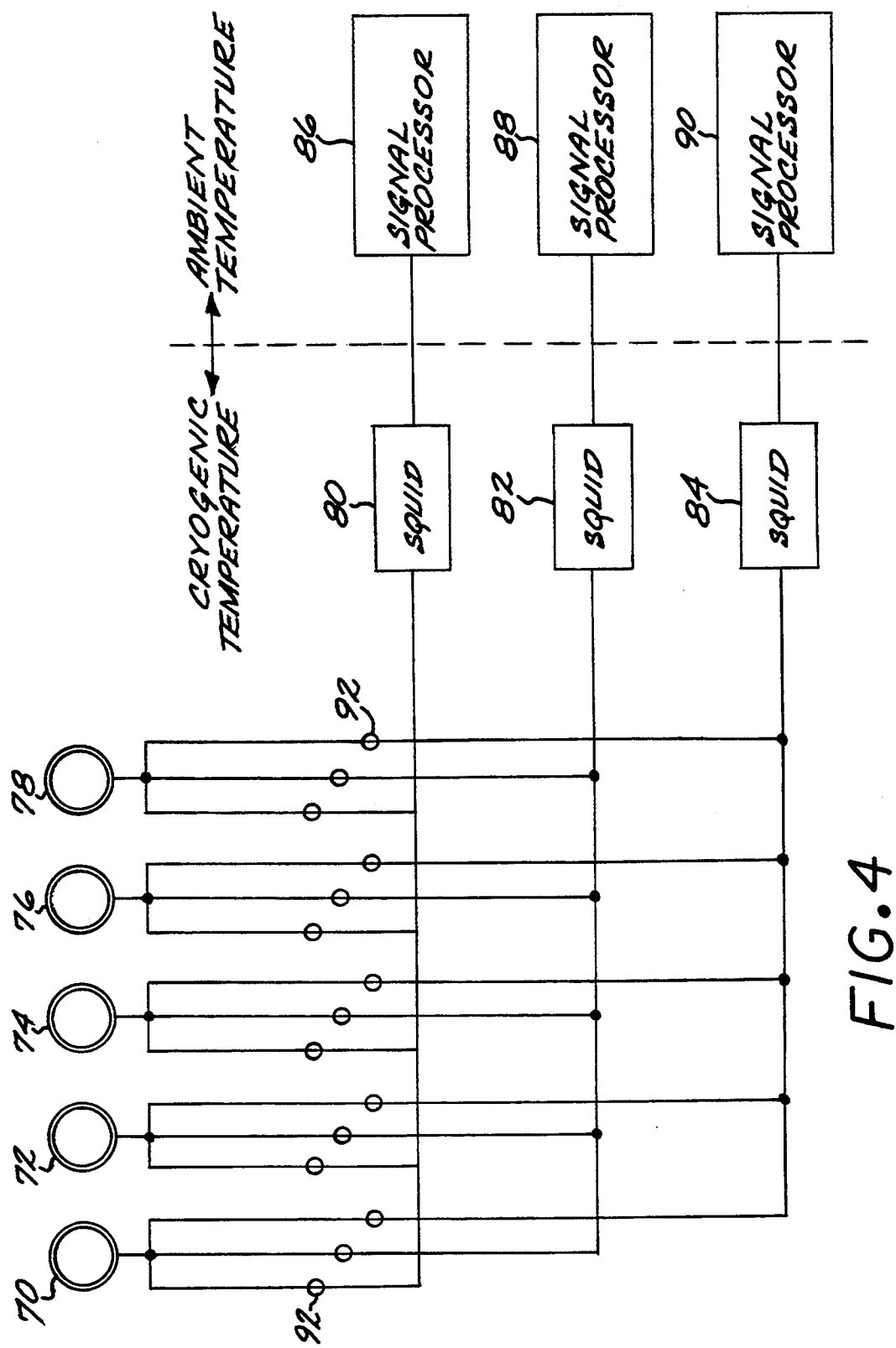

BIOMAGNETOMETER WITH SELECTABLE PICKUP COIL ARRAY

This application is a continuation of application Ser. No. 831,902, filed Feb. 6, 1992, abandoned.

BACKGROUND OF THE INVENTION

This invention relates to the measurement of the small magnetic fields produced by the body of a living organism, and, more particularly, to a biomagnetometer with a large array of pickup coils.

The biomagnetometer is a device that measures the very small magnetic fields produced by the body of a living organism. The magnetic fields, particularly those produced by electrical currents flowing in the brain and the heart, can be important indicators of the health of the body, because aberrations in the magnetic field can be associated with certain types of disfunctions either for diagnosis or early prediction. Moreover, the magnetic fields produced by the brain are an indicator of sensory, motor, or thought processes and the location at which such processes occur, and can be used to investigate the mechanisms of such processes.

Magnetic fields produced by the body are very small, because they result from very small electrical current flows. Typically, the strength of the magnetic field produced by the brain is about 0.00000001 Gauss. By comparison, the strength of the earth's magnetic field is about 0.5 Gauss, or over ten million times larger than the magnetic field of the brain.

The biomagnetometer must therefore include a very sensitive sensor of magnetic fields and sensor channels to process and analyze the output signals of the sensors. Current biomagnetometers utilize a sensor and sensor channel including a pickup coil which produces an electrical current output when a magnetic field penetrates the pickup coil. The electrical current, which is typically very small in magnitude, is detected by a Superconducting QUantum Interference Device, also known by the acronym SQUID. The pickup coil and SQUID normally operate in a superconducting state at reduced temperature. The output signal of the SQUID is provided to ambient-temperature electronics that process and filter the output signal, and thereafter the processed signal is analyzed to determine its relation to the operation of the human body.

Spurious effects from the detection of other magnetic fields than those produced by the brain can be removed by appropriate electronic signal filters. However, the ability of filters to remove all of the extraneous effects is limited. To further improve the signal-to-noise ratio of the system, the subject and pickup coil can be located in a magnetically shielded room.

Over the past 10 years, an important development in the field of biomagnetometry has been an increase in the number of sensors and sensor channels that are available on commercial units. That number has increased from 1 to 7, then to 14 and currently to as many as 37 sensors and sensor channels in a single biomagnetometer. The increase in the numbers of sensors is a highly desirable trend, because the ability to relate the magnetic signals measured by the sensors back to the functioning of the living organism can by improved by the analysis of large arrays of sensor signals, as discussed in U.S. Pat. No. 4,977,896.

As the number of sensors and sensor channels increases, the cost of the biomagnetometer increases accordingly. Although economies of scale and various manufacturing improvements have had some effect on controlling the increase in system costs, in general the larger biomagnetometer systems are much more expensive than the smaller systems. It is likely that future systems with 100 or more sensors and sensor channels will be even more expensive. The development of the field of biomagnetometry and the subsequent availability of this new tool to the general population may be inhibited by the expected large increases in system costs.

There is an ongoing need for an approach to the construction of very large sensor arrays without proportional increases in costs. While improvements in design and manufacturing techniques are helpful, they are not sufficient to reduce the projected systems costs to the extent desired so that large-array biomagnetometers will be priced for widespread use. The present invention fulfills this need, and further provides related advantages.

SUMMARY OF THE INVENTION

The present invention provides a process for obtaining biomagnetic data and a biomagnetometer for collecting magnetic data produced by a living organism. The approach of the invention achieves data acquisition with the power of a large sensor array at a fraction of the cost normally required for such a large array. The accuracy of data collection is greater than possible with conventional equipment. Full-head coverage with a stationary array of sensors is possible at a cost substantially less than if conventional methods were used. The approach also permits general scanning of the biomagnetic output of a portion of the body, and the subsequent focussing of high-resolution data gathering on a region of interest.

In accordance with the invention, a biomagnetometer comprises an array of biomagnetic sensors. The array of sensors comprises a first plurality of magnetic field pickup coils, and a second plurality of detectors, each of which receives a pickup coil output from a pickup coil. The biomagnetometer further includes a third plurality of signal processors, each of which receives an output from a detector, the third plurality of signal processors being fewer in number than the first plurality of pickup coils. There is means for selecting a subset of pickup coils, equal in number to the third plurality of signal processors, from the first plurality of pickup coils for signal processing by the signal processors.

The biomagnetometer has a greater number of pickup coils than signal processors. In one preferred embodiment, there is a detector for each pickup coil, in which case there is a switching capability so that the signal processors may be connected to different subsets of pickup coil/detector combinations. In another embodiment, there is one detector for each signal processor, in which case there is a switching capability so that the signal processor/detector combinations may be connected to different subsets of pickup coils.

In the preferred approach, the pickup coils are formed of one or more turns of materials that are superconducting when cooled below their superconducting transition temperatures. The pickup coils may be wound in various geometric configurations such as magnetometers, axial gradiometers, planar gradiometers, etc. The detectors are preferably superconducting quantum interference devices (known in the art as "SQUIDs") formed of materials that are superconducting when cooled below their superconducting transition temperatures. The signal processors are preferably ambient-temperature electronic circuits, each of conventional design.

The present invention arises from the recognition of the fact that the pickup coils are relatively inexpensive as compared with the signal processors. It is the signal processors that add the greatest cost, per added channel, of large-scale sensor arrays. Each added channel also increases the volume of data that must be processed and analyzed before a result can be displayed. The pickup coils are readily fabricated as large arrays that can provide full-area coverage of a part of the body, but it is comparatively costly to provide a signal processor for each of the pickup coils where the number of pickup coils becomes large. The SQUID detector has an intermediate cost, but the selection of whether a SQUID is provided for every pickup coil relates primarily to the availability of suitable switches that are operable at cryogenic temperature. At the present time switching capability is more readily provided at ambient temperature. It is therefore preferred to have one detector for each pickup coil, and to make the switching between subsets of pickup coils/detectors using ambient-temperature switches.

In accordance with a processing aspect of the invention, a method for gathering biomagnetic information comprises the steps of providing a biomagnetometer including an array of biomagnetic sensors, the array comprising a first plurality of magnetic field pickup coils, and a second plurality of detectors, each of which receives a pickup coil output from a pickup coil, and a third plurality of signal processors, each of which receives an output from a detector, the third plurality of signal processors being fewer in number than the first plurality of pickup coils. The method further includes selecting a subset of pickup coils, no greater in number than the third plurality of signal processors, from within the first plurality of pickup coils for signal processing by the signal processors, and establishing electrical connection from the selected subset of pickup coils, through a detector for each of the pickup coils, and to the signal processors.

The method permits selective focussing of the biomagnetometer on events of interest in the organism. After the initial steps, there may be the additional steps of selecting a second subset of pickup coils from the first plurality of pickup coils for signal processing, and establishing electrical connection from the selected second subset of pickup coils, through a detector for each of the pickup coils, and to the signal processors. Thus, the first subset of pickup coils can be those selected to provide coarsely spaced, low-resolution coverage of a region of interest. Once an event is detected with this large-area array, a second array (usually with the same number of pickup coils) that covers a smaller overall area is selected to provide higher spatial resolution in that specific area. The advantages of both large-area, low-resolution and small-area, high-resolution biomagnetometry are thereby achieved with a single system that costs only marginally more than conventional systems which cover only a small area.

The present invention provides an important advance in the area of biomagnetometry. It permits the number of sensors and sensor channels to be increased to very large numbers while maintaining the total system cost at a reasonable level. System performance is also increased by reduced processing time. And, where low-temperature pickup coil/SQUID switching is available, there is greater cryogenic efficiency and operating costs since fewer electrical leads are required from the interior of the dewar. Other features and advantages of the invention will be apparent from the following more detailed description of the preferred embodiments, taken in conjunction with the accompanying drawings, which illustrate, by way of example, the principles of the invention.

BRIEF DESCRIPTION OF THE DRAWINGS

FIG. 4 is a block diagram of a second embodiment of the invention.

DETAILED DESCRIPTION OF THE PREFERRED EMBODIMENTS

Figure 1:
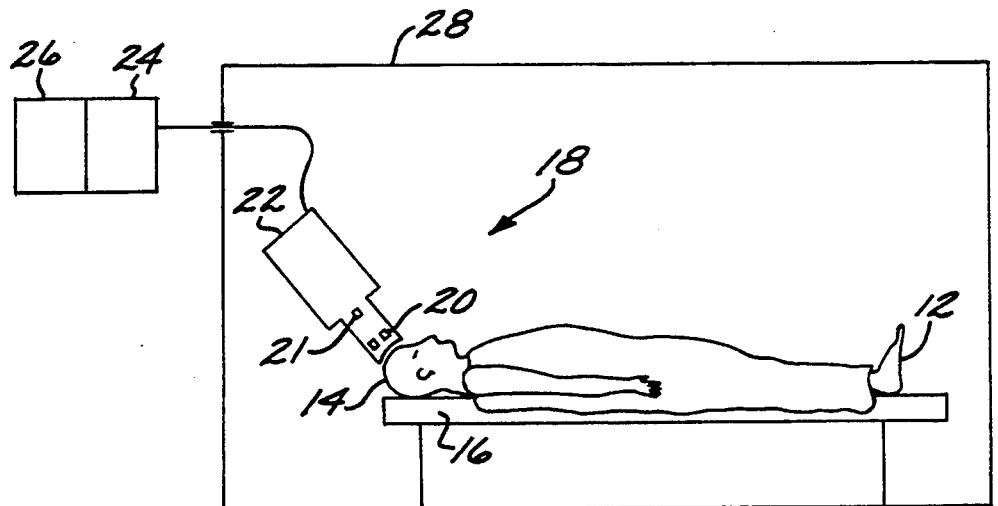
FIG. 1 is a diagrammatic depiction of a biomagnetometer.

As illustrated in FIG. 1, the present invention is preferably embodied in an apparatus 10 for obtaining biomagnetic data from the body 12 of a human patient or subject. More specifically, the data is normally obtained from biomagnetic sources within the head 14 of the person. The person lies upon a table 16 (or sits on a chair) in proximity to a biomagnetometer 18. The biomagnetometer 18 includes a plurality of magnetic field pickup coils 20 for measuring small magnetic fields. The pickup coils may be magnetometers or gradiometers, or of other configuration as may be appropriate for a particular application. In each operating sensor channel, the output signal of the magnetic field pickup coil 20 is detected by a detector, preferably a superconducting quantum interference device 21 (SQUID). Both the magnetic field pickup coil 20 and the SQUID 21 are maintained at a cryogenic operating temperature within a dewar 22. In the preferred practice a large number of sensing coils 20 and SQUIDs 21 are located in the dewar 22.

Figure 2:
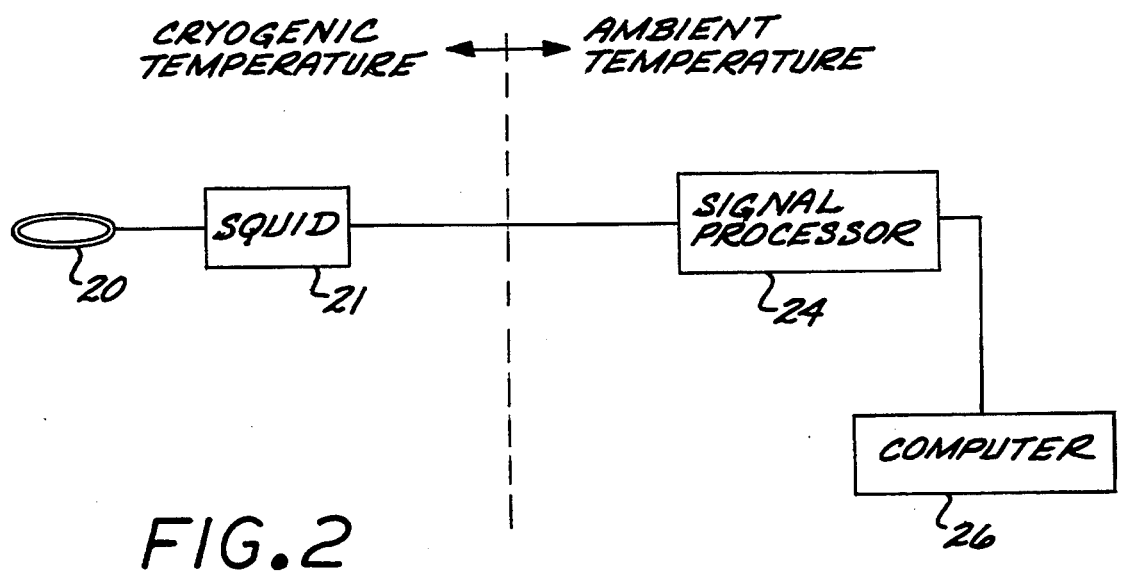
FIG. 2 is a block diagram of a single sensor channel.

The electronics arrangement of the biomagnetometer 18 is illustrated structurally in FIG. 1 and functionally for a single complete sensor channel in FIG. 2. The magnetic signals from the brain are picked up by the magnetic field pickup coil 20 in the dewar 22, which produces a small electrical current output signal when penetrated by a magnetic flux. The output signal of the pickup coil 20 is detected by a detector, in this case the SQUID 21. The SQUID 21 detects the magnetic field flux as an electrical current. The output signal of the SQUID is processed in an ambient-temperature signal processor 24 and stored in a computer 26 as a function of time.

The pickup coil 20 and the body 12 of the patient are preferably, but not necessarily, enclosed within an enclosure 28 (also termed a magnetically shielded room or MSR) that shields the apparatus and magnetic field source from external influences. By screening off the external influences, the amount of signal processing and filtering required to obtain a meaningful indication of the biomagnetic field is reduced.

Biomagnetometers of this general type are available commercially, and their basic structure and operation are known. The operation of SQUIDs and ambient-temperature SQUID electronics are disclosed in U.S. Pat. Nos. 3,980,076; 4,079,730; 4,386,361; and 4,403,189. A biomagnetometer is disclosed in U.S. Pat. No.

4,793,355. Magnetically shielded rooms are disclosed in U.S. Pat. Nos. 3,557,777 and 5,043,529. A signal analysis procedure is disclosed in U.S. Pat. No. 4,977,896. The disclosures of all of these patents are incorporated herein by reference.

In the approach of the invention, there is a first plurality of the pickup coils 20, a second plurality of the SQUIDs 21, and a third plurality of the signal processors 24. The first plurality of pickup coils 20 is larger in number than the third plurality of signal processors 24. The second plurality of SQUIDs 21 may be equal to the number of the first plurality of pickup coils 20 or to the number of the third plurality of signal processors 24, depending upon the system configuration. Two preferred system configurations corresponding to these alternatives are illustrated in FIGS. 3 and 4, respectively.

In accordance with one preferred embodiment, a biomagnetometer comprises an array of biomagnetic sensors, the array comprising a first plurality of magnetic field pickup coils, and a second plurality of SQUID detectors equal in number to the first plurality of magnetic field pickup coils, each of which receives a pickup coil output from a pickup coil. There is further a third plurality of signal processors, the third plurality of signal processors being fewer in number than the first plurality of pickup coils and the second plurality of SQUID detectors, and switch means for switching the outputs of the second plurality of SQUID detectors to the third plurality of signal processors.

Figure 3:
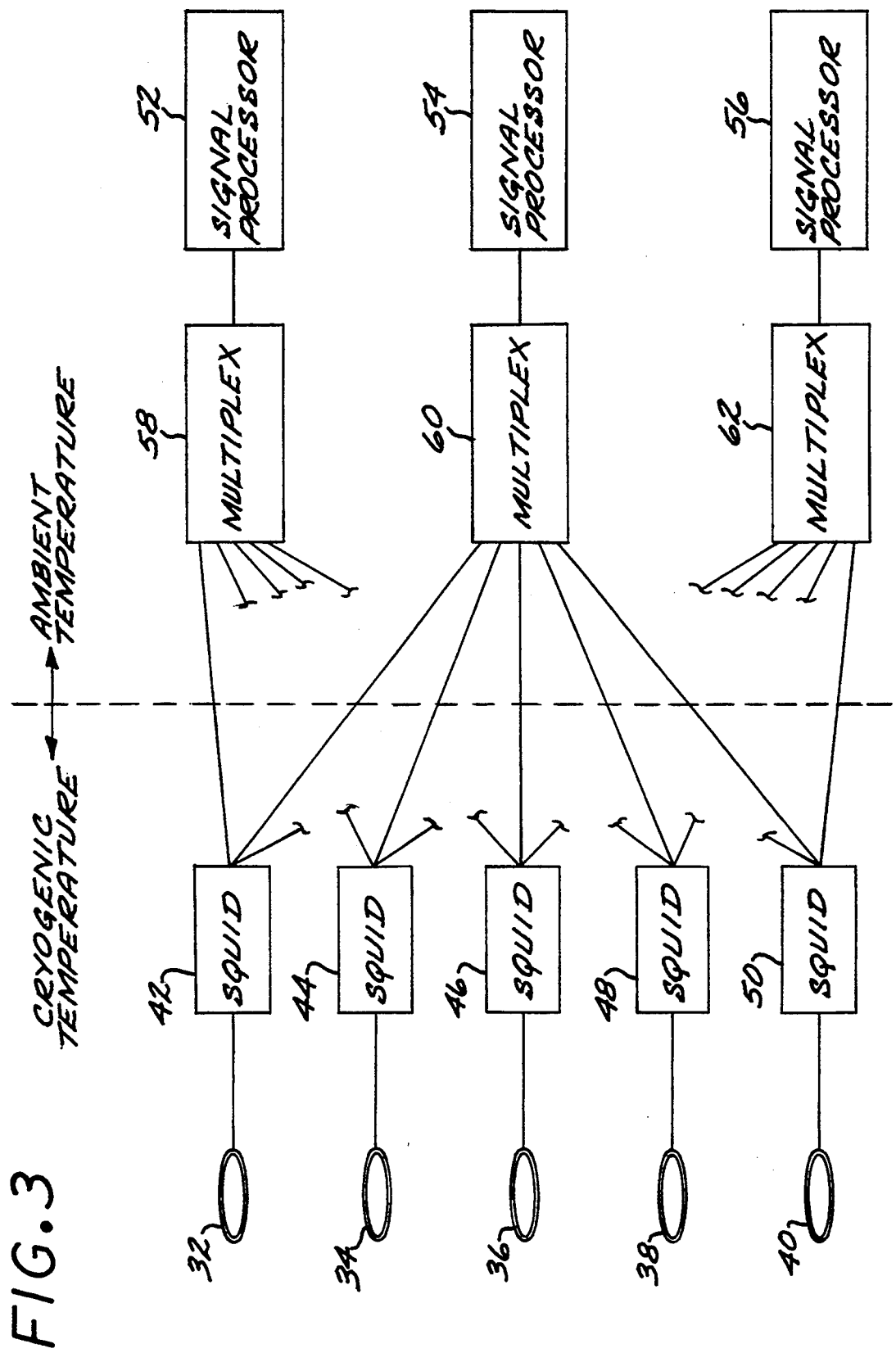
FIG. 3 is a block diagram of one embodiment of the invention.

FIG. 3 presents a block diagram for a biomagnetometer constructed according to this approach. In the illustrated example, a first plurality of pickup coils 32, 34, 36, 38, and 40 is five in number. A second plurality of SQUID detectors 42, 44, 46, 48, and 50 is also five in number. Each SQUID detector 42, 44, 46, 48, and 50 receives the output of a respective one of the pickup coils 32, 34, 36, 38, and 40. (Each pickup coil has two wires extending to it, and each of the lines extending between a pickup coil and a SQUID detector represents these two wires.) The pickup coils and SQUIDs are located within an operable environment, typically a cryogenic environment within the dewar 22.

A third plurality of signal processors 52, 54, and 56 is three in number in this illustration, less than the first plurality of pickup coils and the second plurality of SQUIDs. Each signal processor 52, 54, and 56 receives the output of a multiplexer 58, 60, and 62, respectively. The signal processors and multiplexers operate at ambient temperature.

The input of each multiplexer is connected so that it receives the output of a number of SQUIDs. As shown in FIG. 3, the multiplexer 60 is connected so that it receives the output of each of the SQUIDs 42, 44, 46, 48, and 50, and selectively connects one of those outputs to its signal processor 54. (The multiplexers 58 and 62 are each similarly connected to each of the SQUIDs 42, 44, 46, 48, and 50, but the connection lines are shown in interrupted form in FIG. 3 for the sake of clarity of illustration. These multiplexers 58 and 62 operate in a similar manner to the multiplexer 60.) Equivalently, the multiplexer 60 could be arranged so that it received the outputs of some smaller subset of SQUIDs, such as the SQUIDs 42, 44, 46, and 48, but not the SQUID 50.

Under control of the computer 26, the multiplexer 60 selects one of the outputs of the SQUIDs 42, 44, 46, 48, or 50, and thence the respective signal of the pickup coils connected to the SQUIDs, as input to the signal processor 54. The multiplexers 58 and 62 select the output of others of the SQUIDs for input to their respective signal processors. The result is that the signal processors controllably receive the input of any array of pickup coils at a particular moment.

An example aids in illustrating the utility of this approach. If we suppose that the pickup coils 32, 34, 36, 38, and 40 completely surround the head 14 of the subject, then selection and monitoring of the pickup coils 32, 36, and 40 give a general indication of the presence and origin of a magnetic field signal from the brain. That is, during initial "coarse scale" monitoring the signal processor 52 might process the output from the pickup coil 32, the signal processor 54 might process the output from the pickup coil 36, and the signal processor 56 might process the output from the pickup coil 40.

Once a magnetic field of interest was identified, its character could be evaluated in greater detail by selecting some other combination of pickup coils that would give a more accurate picture of the origin of the magnetic field. The multiplexers would be switched to a combination of pickup coil inputs expected to give a better data set for understanding that event. That is, during a "fine scale" monitoring the multiplexer 58 might be switched so that the output signal of the SQUID 46 is provided to the signal processor 52, the multiplexer 60 might be switched so that the output signal of the SQUID 48 is provided to the signal processor 54, and the multiplexer 62 might be switched so that the output signal of the SQUID 50 is provided to the signal processor 56. In this way, the fields monitored by the pickup coils 36, 38, and 40 could be analyzed, assuming that these three pickup coils are better located to provide information on the character of the event under study in the brain.

This approach is ideally suited to select those arrays of pickup coil signals that can provide the most information, highest resolution, and best signal-to-noise ratio for monitoring particular events. This information is used by array-processing techniques such as that of U.S. Pat. No. 4,977,896. These array-processing techniques are also desirably used in real time to select the combination of pickup coils that provide the best information on the event.

The ability to monitor the living organism over a wide area and then selectively focus on a small area are achieved with a smaller number of signal processors than the number of pickup coils. In the example, there were only five pickup coils and three signal processors. In a commercial unit, it is expected that there would be on the order of at least several hundred pickup coils and fifty or more signal processors. The ratio of pickup coils to signal processors is also expected to be larger in commercial units. That is, there might be a ratio of pickup coils to signal processors of 5:1 or 10:1 in such a commercial unit.

Another embodiment is illustrated in FIG. 4. In this case, there is a first plurality of pickup coils 70, 72, 74, 76, and 78, again five in number in the example. The output of each of the pickup coils is connected to the input of each of a second plurality of SQUIDs 80, 82, and 84, here three in number. The output of each of the SQUIDs 80, 82, and 84 is connected to the input of one respective third plurality of signal processors 86, 88, and 90, here three in number.

Each of the output lines from the pickup coils 70, 72, 74, 76, and 78 to the inputs of the SQUIDs 80, 82, and 84 has a switch 92 therein. The switches 92 interrupt the signal transmission from any pickup coil to any of the SQUIDs. (is in FIG. 3, each line from the pickup coil represents two wires.) The number of switches 92 in this example having a small number of coils is the product of the first plurality times the second plurality, or 15 switches in the illustrated example.

In a preferred approach wherein the pickup coils, SQUIDs, and transmission lines therebetween are operated in the superconducting state, the switches 92 are small heaters that are activated under control of the computer 26. When a heater on a particular line is activated, that line from the pickup coil to SQUID is driven normal (i.e., not superconducting) so that no current passes through the line, effectively opening the switch. With this approach, particular subsets of pickup coils are connected to the SQUIDs 80, 82, and 84. The same types of "coarse scale" and "fine scale" focusing discussed in relation to FIG. 3 are therefore possible with this embodiment.

The difference between the approaches of FIGS. 3 and 4 is that the switching occurs in normal metal lines in the arrangement of FIG. 3 and in superconducting lines in the arrangement of FIG. 4. The latter is more difficult and less cryogenically efficient, but may be preferred in particular circumstances. Selection of one approach or the other will depend upon details of system design. For example, the approach of FIG. 3 requires that more heat-conducting electrical transmission lines extend from the interior of the dewar to the exterior, but the approach of FIG. 4 requires heat input into the switches 92.

The present invention provides an important advance in the field of biomagnetometry. Large arrays of relatively inexpensive pickup coils can be provided, together with smaller numbers of relatively expensive signal processors. Subsets of the large number of pickup coils are selected to meet varying requirements during coarsely and finely focussed analyses of the organism. Although particular embodiments of the invention have been described in detail for purposes of illustration, various modifications may be made without departing from the spirit and scope of the invention. Accordingly, the invention is not to be limited except as by the appended claims.

What is claimed is:

1. A biomagnetometer, comprising:
    an array of biomagnetic sensors, the array comprising
        a first plurality of magnetic field pickup coils, and
        a second plurality of detectors, each of which is functional to detect a pickup coil output, the second plurality of detectors being fewer in number than the first plurality of pickup coils;
    a third plurality of signal processors equal in number to the second plurality of detectors, each of which signal processors is functional to process an output of a single one of the second plurality of detectors; and
    means for controllably selecting a first selected subset of pickup coils, equal in number to the third plurality of signal processors, from the first plurality of pickup coils for signal processing by the signal processors, and thereafter for controllably selecting a second selected subset of pickup coils from the first plurality of pickup coils for signal processing by the signal processors, equal in number to the third plurality of signal processors, for signal processing by the signal processors, the second subset of pickup coils being different from the first subset of pickup coils, the means for controllably selecting in each case being operable to accomplish a connection of each one of the selected subset of pickup coils to a respective one of the detectors, the means for controllably selecting being operable to controllably connect any of the pickup coils to any of the detectors.

2. The biomagnetometer of claim 1, wherein the means for selecting includes switching means for connecting the outputs of the selected subset of pickup coils to the second plurality of detectors.

3. The biomagnetometer of claim 1, wherein at least some of the detectors are superconducting quantum interference devices.

4. The biomagnetometer of claim 1, further including means for analyzing the output signals of an array of pickup coils.

5. The biomagnetometer of claim 1, further including a lead extending between each of the magnetic field pickup coils and each of the detectors, the lead being made of a material that becomes a superconductor at a temperature below a superconducting temperature, and wherein the means for selecting includes
    a heater means associated with each of the pickup coils for controllably heating the respective leads from a temperature below the superconducting temperature to a temperature above the superconducting temperature.

6. A biomagnetometer, comprising:
    an array of biomagnetic sensors, the array comprising
        a first plurality of magnetic field pickup coils, and
        a second plurality of SQUID detectors equal in number to the first plurality of magnetic field pickup coils, each of which receives a pickup coil output from a single one of the pickup coils;
    a third plurality of signal processors, the third plurality of signal processors being fewer in number than the first plurality of pickup coils and second plurality of SQUID detectors; and
    switch means for switching an output of a respective one of each of a subset composed of a third plurality of SQUID detectors, equal in number to the third plurality of signal processors and selected from the second plurality of SQUID detectors, to an input of a respective single one of each of the third plurality of signal processors, the switch means including means for selecting different subsets of SQUID detectors for switching at different times.

7. The biomagnetometer of claim 6, wherein the means for selecting includes means for analyzing the output signals of an array of pickup coils.

8. The biomagnetometer of claim 6, wherein the means for selecting includes
    a multiplexer.

9. The biomagnetometer of claim 6, further including means for cooling the magnetic field pickup coils and the SQUID detectors.

10. A biomagnetometer, comprising:
    an array of biomagnetic sensors, the array comprising
        a first plurality of magnetic field pickup coils, and
        a second plurality of SQUID detectors, the second plurality of SQUID detectors being fewer in number than the first plurality of magnetic field pickup coils;
    a third plurality of signal processors equal in number to the second plurality of SQUID detectors, each of which signal processors receives an output from a single SQUID detector; and switch means for switching an output of a respective one of each of a second plurality of pickup coils, equal in number to the second plurality of SQUID detectors and selected from the first plurality of magnetic field pickup coils, to an input of a respective single one of each of the second plurality of SQUID detectors, the switch means being operable to controllably connect any of the pickup coils to any of the detectors.

11. The biomagnetometer of claim 10, further including means for analyzing the output signals of an array of pickup coils.

12. The biomagnetometer of claim 10, further including means for cooling the magnetic field pickup coils and the SQUID detectors.

13. The biomagnetometer of claim 10, further including a lead extending between each of the magnetic field pickup coils and each of the detectors, the lead being made of a material that becomes a superconductor at a temperature below a superconducting temperature, and wherein the means for selecting includes a heater means associated with each of the pickup coils for controllably heating the respective leads from a temperature below the superconducting temperature to a temperature above the superconducting temperature.

14. A method for gathering biomagnetic information, comprising the steps of providing a biomagnetometer including an array of biomagnetic sensors, the array comprising a first plurality of magnetic field pickup coils, and a second plurality of detectors, each of which detectors is a device whose function is to detect a pickup coil output from a pickup coil, and a third plurality of signal processors, each of which is a device whose function is to process a detector output from a detector, the third plurality of signal processors being fewer in number than the first plurality of pickup coils;

controllably selecting a first subset of pickup coils, no greater in number than the third plurality of signal processors, from the first plurality of pickup coils for signal processing by the signal processors, wherein any of the pickup coils may be selected for processing by any of the detectors;

establishing electrical connection from each one of the selected first subset of pickup coils, through a respective single one of the detectors, and to a respective single one of the signal processors; thereafter controllably selecting a second subset of pickup coils different from the first subset of pickup coils, no greater in number than the third plurality of signal processors, from the first plurality of pickup coils for signal processing by the signal processors, wherein any of the pickup coils may be selected for processing by any of the detectors; and establishing electrical connection from each one of the selected second subset of pickup coils, through a respective single one of the detectors, and to a respective single one of the signal processors.

15. The method of claim 14, including the additional steps, after the step of establishing, of selecting a second subset of pickup coils from the first plurality of pickup coils for signal processing; and establishing electrical connection from the selected second subset of pickup coils, through a detector for each of the pickup coils, and to the signal processors.

* * * * *